(12) United States Patent
Gilmour

(10) Patent No.: US 6,361,515 B1
(45) Date of Patent: Mar. 26, 2002

(54) WALKER

(75) Inventor: Robert Farrer Gilmour, Auckland (NZ)

(73) Assignee: Bodyworks Properties Limited, Auckland (NZ)

( * ) Notice: Subject to any disclaimer, the term of this patent is extended or adjusted under 35 U.S.C. 154(b) by 0 days.

(21) Appl. No.: 09/670,581

(22) Filed: Sep. 27, 2000

Related U.S. Application Data

(62) Division of application No. 09/203,753, filed on Dec. 2, 1998, now Pat. No. 6,155,998.

(30) Foreign Application Priority Data

Dec. 3, 1997 (NZ) .................................................. 329321

(51) Int. Cl.⁷ .......................... A61H 3/00; A43B 13/00; A61F 5/00
(52) U.S. Cl. ................ 602/27; 602/28; 36/95; 36/110; 135/77; 135/82
(58) Field of Search ................ 36/88, 91–95, 36/103, 106, 107; 602/27–30

(56) References Cited

U.S. PATENT DOCUMENTS

| | | | | |
|---|---|---|---|---|
| 2,909,854 A | * | 10/1959 | Edelstein | |
| 3,059,350 A | * | 10/1962 | Price | |
| 3,640,006 A | * | 2/1972 | Kendrick | |
| 4,351,324 A | * | 9/1982 | Bronkhorst | |
| 4,793,078 A | * | 12/1988 | Andrews | 36/43 |
| 5,154,682 A | * | 10/1992 | Kelleran | 36/44 |
| 5,197,942 A | * | 3/1993 | Brady | 602/5 |
| 5,224,277 A | * | 7/1993 | Sang Do | 36/27 |
| 5,233,767 A | * | 8/1993 | Kramer | 36/28 |
| 5,269,748 A | * | 12/1993 | Lonardo | 602/27 |
| 5,329,705 A | * | 7/1994 | Grim et al. | 36/88 |
| 5,370,604 A | * | 12/1994 | Bernardoni | 602/27 |
| 5,429,588 A | * | 7/1995 | Young et al. | 602/27 |
| 5,493,791 A | * | 2/1996 | Kramer | 36/28 |
| 5,735,805 A | * | 4/1998 | Wasserman et al. | 602/10 |
| 5,761,834 A | * | 6/1998 | Grim et al. | 36/88 |
| 5,768,806 A | * | 6/1998 | Parisotto | |
| 5,918,383 A | | 7/1999 | Chee | |
| 6,155,998 A | * | 12/2000 | Gilmour | 602/27 |

* cited by examiner

*Primary Examiner*—Robert Canfield
(74) *Attorney, Agent, or Firm*—Young & Thompson

(57) ABSTRACT

The invention comprises a walker having a frame which provides a bottom and sides. Apertures are provided in the bottom, and a sole piece is positionable adjacent the outer surface of the bottom of the frame in a manner such that parts of the sole piece extend inwardly through the apertures. The inwardly extending parts of the sole piece comprise or include a plurality of protrusions which in use support part of the users foot.

4 Claims, 2 Drawing Sheets

WALKER

Figure 1:
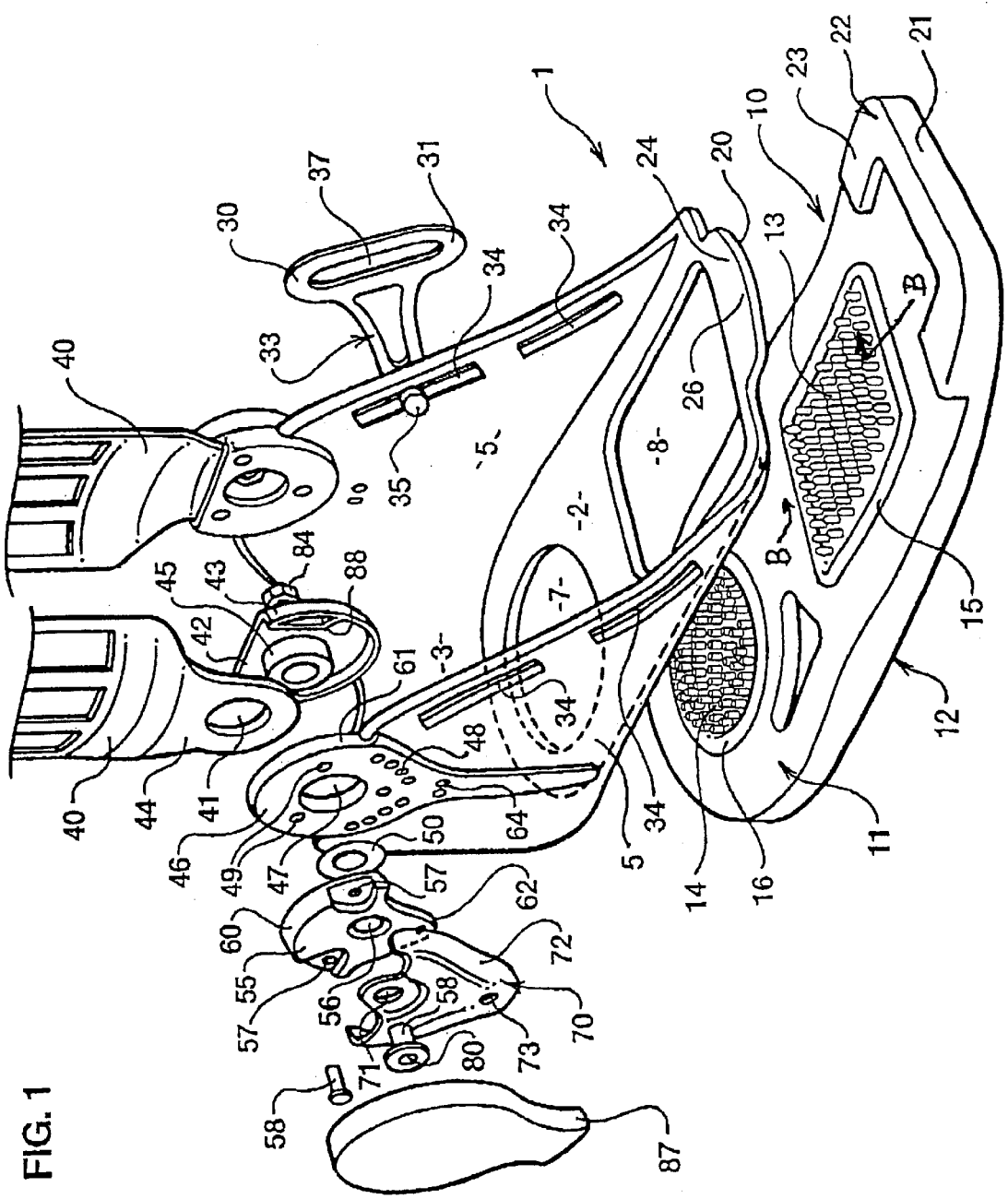

This application is a divisional of application Ser. No. 09/203,753, filed on Dec. 2, 1998, now U.S. Pat. No. 6,155,998 the entire contents of which are hereby incorporated by reference.

This invention relates to a walker particularly an orthopaedic walker.

With orthopaedic walkers it is desirable that the comfort to the user be increased wherever possible so as to place minimum restrictions on the user. It is also desirable that the walker allows a walking motion as close to that of normal walking as possible.

Furthermore it is desirable in many cases that some movement of the ankle joint be allowed and that the range of such movement be able to be substantially controlled.

It is also desirable that pressure relief is available. Attempts have been made to achieve that by removing areas of the footbed lining. However such an approach can encourage herniation of the soft tissue into the moved space which can result in margination or restricted blood flow around the edges of the deficit. Thus there remains a need to provide a walker able to provide pressure relief but also able to reduce or eliminate margination.

It is therefore an object of the present invention to provide in its various embodiments a walker which will go at least some way towards meeting at least some of the foregoing desiderata in a simple yet effective manner or which will at least provide the public with a useful choice.

Accordingly, in one aspect the invention consists in a walker comprising a frame providing at least a bottom and sides, apertures in the bottom, and a sole piece positionable adjacent the outer surface of the bottom of the frame in a manner such that parts of the sole piece extend inwardly through the apertures, the inwardly extending parts comprising or including a plurality of protrusions.

Preferably the protrusions are positioned in use under the heel and/or the ball of the foot of the wearer of the walker.

Preferably there are substantially three to substantially ten protrusions per centimetre squared.

Preferably there are four to five protrusions per centimetre.

If desired some protrusions can be removed to provide pressure relief in use.

Preferably a lining is provided over said protrusions.

Preferably the sole piece extends forwardly of the foremost parts of the frame bottom, so that in use, at least part of the toes of the user of the walker are adjacent the sole piece.

Preferably the sole piece has a ridge at or adjacent its forward edge in use so that the upper edge of the ridge lies substantially in the same plane as the upper surface of the frame bottom.

Preferably the walker further includes one or more arms engaged or engageable with the frame, connection means between the or each arm and the frame, the or each connection means including a range of motion device.

Preferably the range of motion device is adjustable as to the range of movement.

Preferably the walker further includes one or more chafes mounted on the frame, the or each said chafe having an apertured section to receive a strap or the like, a mounting section engageable on the frame, and a linking section linking the apertured section and the mounting section, at least the linking section being flexible such that in use the chafe will be positioned closely to a foot within the walker.

In a further aspect the invention consists in a method of reducing margination in a walker comprising the steps of; providing a walker chassis, providing a weight bearing surface for a users foot and associated with the chasis, and removing a selected part or selected parts of the weight bearing surface so that in use the sole of the users foot has areas which are positioned above the weight bearing surface but are not supported by the weight bearing surface preferably a lining is provided over the weight bearing surface.

To those skilled in the art to which the invention relates, many changes in construction and widely differing embodiments and applications of the invention will suggest themselves without departing from the scope of the invention as defined in the appended claims. The disclosures and the description herein are purely illustrative and are not intended to be in any sense limiting.

Figures 2, 3, 4, 5, 6:
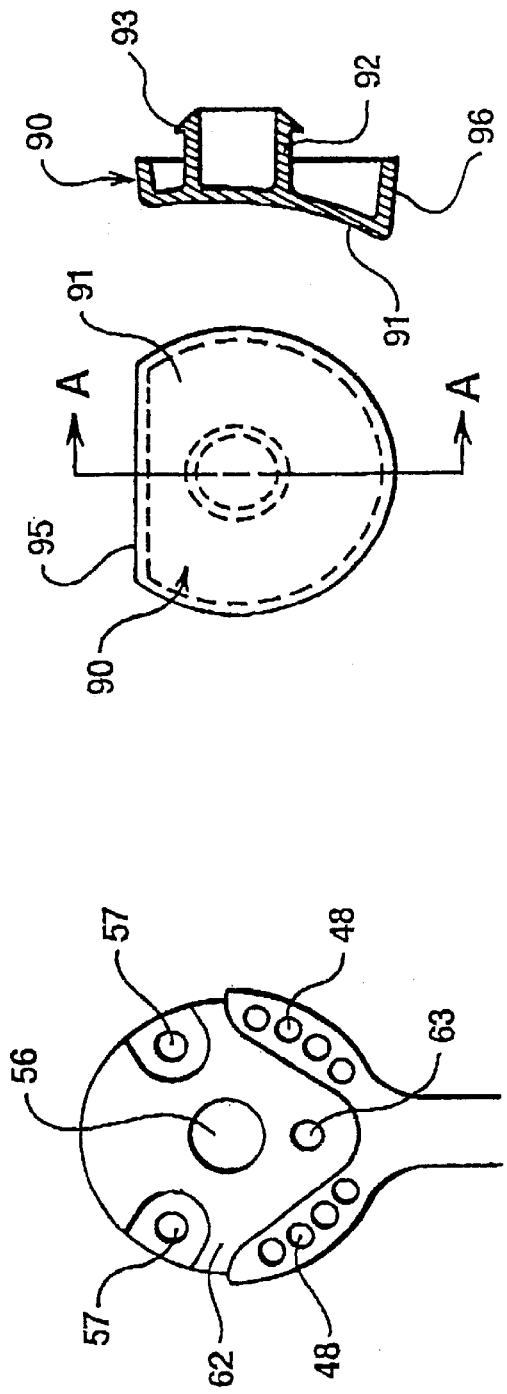

One preferred form of the invention will now be described with reference to the accompanying drawings in which, FIG. 1 is a diagrammatic exploded view of a walker according to various embodiments of the invention, with the internal liner not shown for clarity, FIG. 2 is a front elevation of parts of a range of motion device usable in aspects of the invention, FIG. 3 is a front elevation of a cushioning pad useable in aspects of the walker according to the invention, FIG. 4 is a cross-section on a "A—A" in FIG. 3., FIG. 5 is a diagrammatic front elevation of a chafe according to one form of the invention, and FIG. 6 is a diagrammatic cross-section on B—B in FIG. 1 with some protrusions removed.

In the preferred form of the invention a walker is provided which has a frame 1 which includes a bottom plate 2. The bottom plate has a rear part 3 which provides a back heel plate and also side plates 5 extending upwardly from the bottom plate 2. The chassis is made from a metal or suitable durable plastics material. Generally the parts 2, 3, 5 will be formed as an integral item.

A weight bearing surface is associated with the frame 1. To this end the bottom plate 2 includes apertures such as heel aperture 7 and ball aperture 8. The size of these apertures is desirably such that the heel of a user and the ball of the foot of the user will be placed within the boundaries of the apertures. The weight bearing surface is provided by a sole piece 10 formed of a suitably hard wearing but stiffly resilient material such as a suitable plastics or rubber material and the sole has an upper surface 11 and a lower surface 12. Plastics and rubber materials of this type are known in the footwear industry. The lower surface 12 is shaped and configured so as to provide the desired walking or motion characteristics of the walker.

The upper surface 11 includes parts which extend upwardly through the apertures 7 and 8 in the walker bottom plate 2. Thus in the embodiment described a plurality of protrusions 13 extend through aperture 8 and a plurality of protrusions 14 extend through apertures 7. The protrusions are formed of the same material as the sole 10 and may be surrounded in each case with a peripheral ridge 15 or 16 so as to locate the sole accurately within the cut-out area 7 or 8. The protrusions 13 desirably have a rounded distal end. A liner 17 is placed over the bottom plate 2 and protrusion sets 13 and 14 to provide an interface with the users foot.

In use the protrusions absorb impact and conform to the weight bearing surface of the foot, that is to say they adapt to the shape of the foot. Because of the flexibility or deformability or both, the protrusions of the walker become left or right sided with preserves the natural biomechanics of the foot. It also reduce or eliminates lateral shear stress, that is to say, the foot does not "shimmy" from side to side.

The protrusions could comprise a brush like construction. That is to say the protrusion could be fine in nature. However we believe a brush like structure may be less stable than the protrusions described above.

In the preferred forms of the invention some of the protrusions 13(a) could be selectively removed to provide pressure relief for, for example, a foot ulcer. The construction also does not build up the heel height when used with an apertured walker which prevents or minimises any tendency tissue herniation and margins of reduced vascularity. That is the liner 17 is intact and does not create an aperture which could lead to herniation.

The liner 17 may be constructed so that the parts 17(a) which lie adjacent the weight bearing surface are softer. Thus these parts could contain a soft silicon or a gel or could simply be formed of softer material. The harder remaining part 17(b) will keep the liner sufficiently stable for use. Where soft silicon or a gel is used, these can be "welded" into a pocket in the liner body. By inserting different gels or interface material degrees of pressure relief can be obtained.

The softness, size and number of provisions are empirically derived and could vary depending on the age and size for example of the user. Between approximately three and ten protrusions per centimetre squared could be expected, for example in the range of four or five, but as stated above the actual number is empirically derived.

The front edge 20 of the bottom plate 2 stops short of the extent of the toes of the user when in use. That is to say the user toes will extend beyond the forward edge of the bottom plate 2. To accommodate this the front edge 21 of the sole 10 is built up into a ridge 22 which in use is positioned adjacent the front edge 20 of the bottom plate 2. The top surface 23 of the ridge 22 is preferably substantially coplanar or lies substantially in the same plane as the top edge 24 of the bottom plate 2.

In the embodiment shown in FIG. 1 the bottom plate 2 has a central tongue 26 which is positioned into the substantially U shaped ridge 22. In use the toes of the user extend outwardly onto the ridge 22. This construction provides a degree of flexibility in the front of the foot thus when a gait is initiated the toes are enabled to bend and thus there is sufficient lift of the pelvis to allow the foot to swing through. The degree of flex reduces the pelvic tilt required to initiate the swing phase of movement and assists in initiating that swing phase as the recoil of the sole returns the stored potential energy of flexible to at least some extent thus assisting in propelling the foot forwardly. The sole in the area of the ridge 22 must be reasonably stiff yet allow flexing to occur. The stiffness required is empirically derived.

A chafe 30 is provided which has a mounting part 32 a strap engaging part 31 and a link 33. The chafe is desirably formed of a flexible and preferably resilient material such as for example a suitable grade of polyurethane although other materials can be used. An aperture 36 is provided through which the chafe may be engaged with the frame for example by a fixing pin 35 running in slots 34. The slots may be replaced by single apertures if desired. The pins may carry threads and be secured by a suitable not or otherwise as desired.

An elongated aperture 37 is provided at the fixing or apertured part through which a strap may be positioned. FIG. 1 is shown with a single chafe but of course a pair of chafes on opposite sides of the frame or four chafes can be provided to be secured by a strap interconnected for example by hook and loop pad constructions such as that sold by reference by the trade mark VELCRO. The link 33 of the chafe is preferably formed by a pair of arms 38 and 39 as can be seen in FIG. 5.

Because of the flexible nature of the chafe in use it will conform to the shape of the users foot by bending and twisting as necessary. This is aided by the provision of the two flexible arms.

The close fit increases the comfort for the user and also aids in providing a suitable tight engagement of the frame to the wearers foot. One or more, preferably a pair, of arms 40 are engaged with the frame 1 and this is density through a suitable range of motion device.

To this end the arm 40 as its lower end has an aperture 41. An inner plate 42 is provided which has a peripheral rib 43 open at the top end so that the arm may pass out past the rib in the region 44 of the arm.

Extending inwardly is a shaft 45 having a central bore. The shaft 45 passes through the aperture 41 and the arm 40 and also through an aperture 47 in a protusion 46 carried by the frame 1. The construction is such that the inner plate 42 moves with the arm 40.

The shaft passes completely through the central aperture 47 and mounts a washer 50. The protrusion carries a pair of apertures 49 the use of which will be described later hereinafter and also beneath the protrusion is provided two sets of apertures 48 through which range of motion pins may be inserted in a desired one of the selected positions.

A first outer plate 55 is provided which has a peripheral rim 60 which fits against the outer edge 61 of the protrusion 46. Pins 58 pass through apertures 57 in the outer plate and into the apertures 49 to secure the outer plate to the protrusion 46. A central aperture 56 is provided in the first outer plate 55 which also has a downwardly depending portion 62 with an aperture 63 therein.

A second outer plate 70 is provided which has a similar downwardly depending part into which is provided an aperture 73 so that a pin may pass through the aperture 73 the aperture 63 and a suitable one of apertures 64 provided in the frame. A central aperture 71 is also provided in the outer cover through which a pin 80 is provided which passes through the aperture 71 the aperture 56 and into the shaft 45 to be secured by nut 84 which is desirably trapped within the inner parts of the shaft 45.

An outer cover 87 is provided to cover the whole mechanism.

The second outer plate 58 also has a peripheral rim 72 to make a suitably positioned fit over the inner plate 55.

In use the outer cover 87 is removed and the pins (not shown) in selected apertures 48 are if desired re-positioned in the desired apertures 48.

The inner plate 42 is shaped to provide a pair of shoulders 88 which as they rotate strike against the pins in the apertures 48. Therefore by suitably positioning the pins 48 the range of motion may be varied.

An inner cushion pad is desirably provided by pad 90 which desirably is slightly concave. The rear face of the pad 90 is slightly concave on its outwardly facing face. The inner face has a protrusion 92 carrying peripheral catch 93. The top edge of the cushion pad 95 is cut in the form of a segment as can be seen in FIG. 3 so as to match the shape of the inner plate 42.

The peripheral rim 96 is also provided for accurate positioning of the cushioned pad which may be formed of any suitable material such as for example a soft polyurethane or the like.

In use the range of motion pins in the apertures 48 are able to be shifted as desired by removing the final outer cover 87 to gain access to the pins.

Thus it can be seen that at least in the preferred form of the invention a walker is provided that has in each of its embodiments a number of advantages particularly in the area of user comfort.

The apparatus is also efficient to produce and effective in use.

I claim:

1. A method of reducing margination walker comprising the steps of:

providing a walker chassis;

providing a weight bearing surface for a user's foot and associated with the chassis, the weight bearing surface being provided with a plurality of protrusions;

removing a selected part or selected parts of the weight bearing surface; and providing a lining over the weight bearing surface, including the removed part or parts, so that in use a sole of a user's foot has areas which are positioned above the weight bearing surface but are not supported by the weight bearing surface, the user's foot contacting the lining.

2. The method as claimed in claim 1, wherein the protrusions are spaced apart.

3. A method of reducing margination in a walker, comprising the steps of:

placing a user's foot in a walker chassis that has at least one aperture in a bottom thereof;

supporting the user's foot on a multiplicity of spaced-apart dimples that project through said aperture; and reducing a height of a selected number of said multiplicity of spaced-apart dimples to provide an area of reduced support for the user's foot.

4. The method of claim 3, further comprising the step of covering said multiplicity of space-apart dimples with a lining.

* * * * *